United States Patent
Kim et al.

(10) Patent No.: US 7,097,967 B2
(45) Date of Patent: Aug. 29, 2006

(54) METHOD OF PREDICTING DRUG-FOOD INTERACTION

(75) Inventors: Aeri Kim, Daejeon (KR); Kwan Hyung Cho, Daejeon (KR); Sun Hwa Lee, Daejeon (KR); Suk Kyoon Yoon, Daejeon (KR); Hee Dong Park, Daejeon (KR); Kyung Ha Chung, Daejeon (KR); Ho Jun Kim, Daejeon (KR); Han Joo Maeng, Incheon (KR); Tae Hun Kim, Daejeon (KR); Bong Chan Kim, Daejeon (KR); Sung Ji Kim, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 391 days.

(21) Appl. No.: 10/280,587

(22) Filed: Oct. 24, 2002

(65) Prior Publication Data

US 2004/0081641 A1 Apr. 29, 2004

(51) Int. Cl.
*C12Q 1/00* (2006.01)
(52) U.S. Cl. .............................. 435/4; 424/9.1; 424/9.2
(58) Field of Classification Search .................. 435/4, 435/23, 375; 424/9.1, 9.2
See application file for complete search history.

(56) References Cited

U.S. PATENT DOCUMENTS

| | | | |
|---|---|---|---|
| 5,294,615 A | 3/1994 | Meyer et al. | 514/254 |
| 6,013,680 A * | 1/2000 | Ogawa et al. | 424/94.63 |
| 6,338,857 B1 | 1/2002 | Seth | 424/464 |
| 6,368,628 B1 | 4/2002 | Seth | 424/480 |
| 2002/0094346 A1* | 7/2002 | Lin | 424/490 |
| 2003/0118547 A1* | 6/2003 | Vandenberg | 424/85.4 |
| 2004/0229821 A1* | 11/2004 | Kim et al. | 514/19 |

FOREIGN PATENT DOCUMENTS

WO 00/39124 7/2000

OTHER PUBLICATIONS

Vallez M. Different Food Interactions for the Orally Active Thrombin Inhibitors S 18326 and S 31922 In Dogs. Poster 2289 XVIIth Congress of the International Society For Thrombosis & Haemostasis, Washington, DC. 1999.*
Carver, P.L., et al., "Meal Composition Effects on the Oral Bioavailability of Indinavir in HIV-Infected Patients," *Pharmaceutical Research*, vol. 16, No. 5, pp. 718-724 (1999).
Charman, W.N., et al., "Physicochemical and Physiological Mechanisms for the Effects of Food on Drug Absorption: The Role of Lipids and pH," *Journal of Pharmaceutical Sciences*, vol. 86, No. 3, pp. 269-282 (Mar. 1997).
Fleisher, D., et al., "Drug, Meal and Formulation Interactions Influencing Drug Absorption After Oral Administration," *Clin. Pharmacokinetics*, vol. 36, No. 3, pp. 233-255 (Mar. 1999).
Garty, M. and A. Hurwitz, "Effect of cimetidine and antacids on gastrointestinal absorption of tetracycline," *Clin. Pharmacol. Ther.*, vol. 28, No. 2, pp. 203-207 (Aug. 1980).
Gustafsson, D., et al., "The Direct Thrombin Inhibitor Melagatran and Its Oral Prodrug H 376/95: Intestinal Absorption Properties, Biochemical and Pharmacodynamic Effects," *Thrombosis Research*, vol. 101, pp. 171-181 (2001).
Hoffken, g., et al., "Pharmacokinetics and Bioavailability of Ciprofloxacin and Ofloxacin: Effect of Food and Antacid Intake," *Rev. Infect. Dis.*, vol. 10, pp. S138-S139 (1988).
Kane, G.C. and J.J. Lipsky, "Drug-Grapefruit Juice Interactions," *Mayo Clin Proc.*, vol. 75, pp. 933-942 (2000).
Luciano, V.S., *Human Physiology*, 5th edition, Chapter 16, pp. 526-545 (1990).
Pao, L-H., et al., "Reduced Systemic Availability of an Antiarrhythmic Drug, Bidisomide, with Meal Co-Administration: Relationship with Region-Dependent Intestinal Absorption," *Pharmaceutical Research*, vol. 15, No. 2, pp. 221-227 (1998).
Rowland, M. and T.N. Tozer, *Clinical Pharmacokinetics: Concepts and Applications*, Chapter 17, pp. 246-248 (1980).
Schmidt, L.E. and K. Dalhoff, "Food-Drug Interactions," *Drugs*, vol. 62, No. 10, pp. 1481-1502 (2002).
Shuman, R.T. and P.D. Gesellchen, "Development of an Orally Active Tripeptide Arginal Thrombin Inhibitor," *Pharmaceutical Biotechnology*, vol. 11, *Integration of Pharmaceutical Discovery and Development*, pp. 57-80, no date given.
Singh, B.N., "Effects of food on clinical pharmacokinetics," *Clinical Pharmacokinetics*, vol. 37, No. 3, pp. 231-255 (1999).

(Continued)

*Primary Examiner*—Ralph Gitomer
(74) *Attorney, Agent, or Firm*—Ladas & Parry LLP

(57) ABSTRACT

The present invention provides a method of predicting a food-drug interaction in vivo, in the case of an orally administered drug interactive with digestive enzymes in the gastrointestinal tract, by measuring the activity of the drug to the digestive enzymes in vitro, which is based on the fact that the ingestion of foods causes the absorption of drug in vivo to decrease due to the above interaction between a drug and digestive enzymes. The present invention further provides methods of minimizing the change of absorption in vivo caused by the ingestion of foods by reducing the action of digestive enzymes, for example, introduction of prodrugs, modification of the chemical structure of drug, design of drug formulation, etc.

4 Claims, 1 Drawing Sheet

OTHER PUBLICATIONS

Vallez; M-O, et al., "Different food interaction for the orally active thrombin inhibitors S 18326 and S 31922 in dogs," *Poster 2289, XVIIth Congress of the International Society for Trombosis and Haemostasis*, Washington D.C. (1999).

* cited by examiner

METHOD OF PREDICTING DRUG-FOOD INTERACTION

TECHNICAL FIELD

The present invention relates to a method of predicting a food-drug interaction in vivo by measuring the activity of a pharmaceutical drug to digestive enzymes in vitro, based upon the phenomenon that, in cases where an orally administered drug interacts with digestive enzymes in the gastrointestinal tract, ingestion of the foods causes the decrease of drug absorption rate in vivo, which was first observed by the present inventors. The present invention further relates to methods of minimizing the change of drug absorption rate in vivo, caused by the ingestion of foods, by reducing the interaction with the digestive enzymes, for example, introduction of prodrugs, alteration of drug structures, design of drug formulations, and the like.

BACKGROUND OF THE INVENTION

The most convenient method of administering medications to patients is generally to administer the drugs orally. The extent of bioavailability in the same medication may vary from one individual to another, and such difference in the bioavailability is caused by differences in the extent of absorption, metabolism and excretion in human subjects. Changes in bioavailability of the same medication may occur even with the same patient; for example, when the medication is taken together with another medication or foods.

Drug-drug interaction, i.e., when a medication is concurrently administered with another medication, and the in vivo absorption rate of a certain medication changes, has been well known, and the mechanism thereof varies depending on the kind of medications. For example, there are the case that a medication accelerates or inhibits a gastric empting rate, thereby changing the absorption of another medication; the case that a medication has an effect on the medication metabolism in the liver, thereby changing the bioavailability of another medication; and the case that a patent's metabolism exhibits varying rates of the excretion of another medication from the kidney, thereby changing the bioavailability of another medication. (Clinical Pharmacokinetics. Concepts and Applications, M. Rowland and T. N. Tozer, Chapter 17. Drug Interactions., 1980, Lea & Febiger). There are various examples, especially, where the change of medication absorption in human subjects is caused by the change of medication metabolism; therefore, in the preparation procedure of a novel medication, it is required to identify the types of medications which should not be concurrently administered with this medication, according to the drug-drug interaction studies.

As another factor affecting bioavailability, the ingestion of foods has been reported, and the representative example thereof is the change of bioavailability of medications, such as cyclosporine, Ketoconazole and the like, caused by ingestion of a grapefruit juice. From this study, it was found that the medication metabolism is reduced by ingestion of grapefruit juice, whereby the bioavailability of the medication increases. The medication metabolism enzymes involved in such phenomenon in a liver were also identified (G. C. Kane and J. J. Lipsky 2000. *Mayo Clin. Proc.* 75(9) 933–42).

Generally, food-drug interaction means the change of the bioavailability of medications or drugs caused by intake of foods, and can unintentionally reduce or increase the effect of drug, resulting in therapeutic failure or increased toxicity. This may adversely affect patient care, contribute to morbidity and long treatment time or hospitalization. (L. E. Schmidt and K. Dalhoff, *Drugs* 2002. 62(10). 1481–1502). For this reason, FDA recommends to test bioequivalency of drug products either under fasted or fed conditions, and for the latter case the meal itself is standardized (Guidance for industry. Food-Effect Bioavailability and Bioequivalence studies).

The mechanism of the food-drug interaction depends on, in addition to the metabolism as mentioned above, physicochemical factors, physiological factors, compositions of foods, compositions of drugs, and combinative factors thereof (D. Fleisher et al., *Clin. Pharmacokinetics* 1999. Mar. 36(3). 233–254; W. Charman et al., *J. Pharm. Sci.* 1997. 86(3). 269–282).

The dissolution rate of a medication, being one of innate physicochemical properties of the medication, is an important factor having an effect on the food-drug interaction. When the solubility of a medication significantly depends on a pH of a solution, the dissolution rate varies with the change of pH in a gastrointestinal tract caused by ingestion of foods, whereby the absorption rate of the medication can change.

Indinavir ([1(1S,2R), 5(S)]-2,3,5-trideoxy-N-(2,3-dihydro-2-hydroxy-1H-inden-1-yl)-5-[2-[[(1,1-dimethylethylaminocarbonyl)-4-(3-pyridinylmethyl)-1-piperazinyl]-2-(phenylmethyl)-D-erytho-pentonamide sulfate (1:1) salt], a drug for treatment of AIDS, is a well known example of a case where the absorption rate of a medication changes in accordance with the change of dissolution rate thereof, and it has been reported that the absorption rate decreases when the drug is administered together with foods. For this reason, this medication should be administered one hour prior to meals or two hours after meals. As a mechanism illustrating how the absorption rate of this medication decreases upon ingestion of foods, it has been known that the dissolution rate of a weakly acidic medication decreases as the pH of gastric fluids rises (P. L. Carver et al., 1999, *Pharm. Res.* 16(5) 718-).

For tetracycline and fluoroquinoline-based antibiotics, it has been known that the absorption thereof is diminished upon binding with metallic ions contained in foods (M. Garty and A. Hurwitz, 1980 *Clin. Pharmacol. Ther.* 28. 203–207; G. Hoffken et al. 1988. *Rev. Infect. Dis.*, 10, 138–139). For some of liposoluble medications with very low solubility, the dissolution time increases due to the delay of a stomach emptying time following ingestion of foods, or its solubility in bile upon secretion of the bile increases, whereby the absorption rate of the medication increases (L. E. Schmidt and K. Dalhoff, *Drugs* 2002. 62(10). 1481–1502).

If the mechanism of the food-drug interaction of a certain medication is found, it may be possible to change the bioavailability thereof by designing its drug formulation to minimize the interaction. For example, in the case that the solubility of medication is a key factor affecting the food-drug interaction, the effect of foods can be minimized by designing the drug formulation which increases the solubility of medication. For example, the crystalline structure of medication may have an effect on the dissolution rate, so that a method has been known of reducing the absorption change caused by foods, by changing the crystalline structure (U.S. Pat. No. 5,294,615).

However, among medications which have a high solubility but are absorbed only at a specific site, especially, in the proximal region of the small intestine, or have a low membrane penetration rate, many medications show a decreased absorption rate upon food ingestion. U.S. Pat. No. 6,338,857 and U.S. Pat. No. 6,368,628 claimed a novel sustained release composition free of food effect. However, these patents do not suggest any mechanism to prevent food effect. Also, in the case of medications which have little room to be improved by the design of novel drug formulation, it has been known that the membrane penetration rate can be improved by altering the molecular structure of the medication itself (Pao et al., *Pharm. Res.* 1998: 15(2) 221–227).

As mentioned above, even though a plurality of complicated physicochemical, physiological factors have been known regarding the mechanisms of food-drug interaction, it has not been possible to predict the food-drug interaction from the chemical structure or type of a certain medication (B. N. Singh, *Clinical Pharmacokinetics* 1999. 37:3, 213–255). However, the present inventors first found an interaction between drugs and digestive enzymes, being a novel mechanism of the food-drug interaction, which has never been known in this art.

SUMMARY OF THE INVENTION

Figure 1:
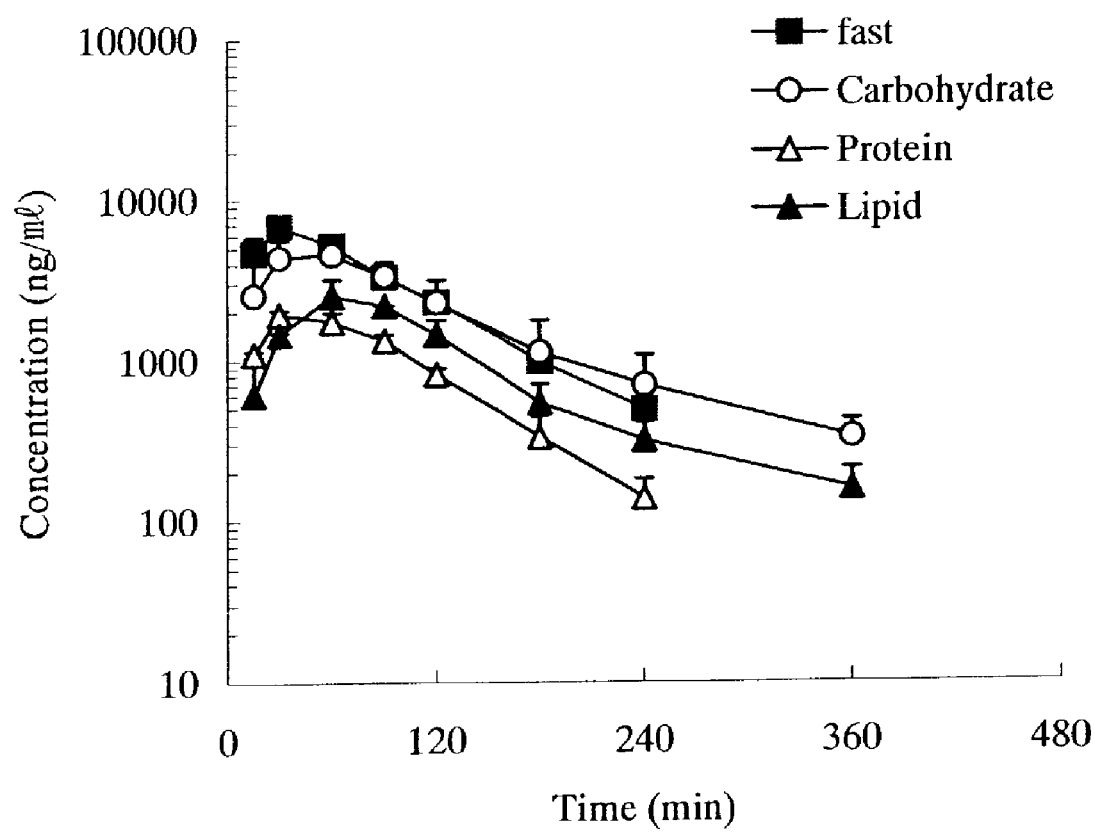
FIG. 1 is a graph showing the serum levels of Drug A when administering the drug to laboratory dogs in a fasting state and after feeding of carbohydrate, protein and lipid, respectively.

Accordingly, the present invention provides a method of predicting a food-drug interaction in vivo, where a drug appears to be able to react with digestive enzymes in view of their structures, by measuring the activity of the digestive enzymes to the drug in vitro. Furthermore, the present invention provides, on the basis of such prediction of the food-drug interaction, methods of reducing the interaction of the drug to the digestive enzymes to counter the decrease of the drug absorption caused by ingestion of foods, for example, introduction of prodrugs, design of formulations, etc.

Said digestive enzymes are the enzymes, involved in digestion, being secreted from a gastrointestinal tract, and include, for example, trypsin, chymotrypsin, carboxypeptidase, lipase, amylase, ribonuclease, deoxyribonuclease, etc. The activity of drug to one or more digestive enzymes selected from the above can be measured. Especially, according to the present inventors' study, trypsin was ascertained to have a significant effect on dereasing the activity of thrombin inhibitors.

Said drug is not particularly limited if it is an orally administrable drug, and its representative example is a peptidometic-based serine protease inhibitor. The preferred examples of said serine protease include thrombin inhibitors, Factor Xa inhibitors, Factor VIIa inhibitors, etc. and the thrombin inhibitors are particularly preferred among them. Said drug may generally be one of nucleic acid derivatives, and since the nucleic acid derivatives-based drugs have been known in the art, the detailed description thereof is omitted in the present specification.

Methods of measuring the activity of drug to the digestive enzymes in vitro include the known ones in the art to which the present invention pertains, and these methods are incorporated into the present invention as a reference. One embodiment of the activity-measuring methods is illustrated in the Experimental Example 2.

Furthermore, the present invention provides methods of reducing the activity of a drug to digestive enzymes to improve the food-drug interaction, by predicting the food-drug interaction from the measurement of the activity of drug to digestive enzymes in vitro.

A variety of methods can be applied to reduce the activity of drug to the digestive enzymes, for example, a method of altering the molecular structure of drug, a method of using prodrugs, a method of using drug formulations designed to decrease the enzymatic action, etc., but the present invention is not limited to them. An embodiment of altering the molecular structure of a drug is to change groups of a high activity to less active or non-reactive groups, depending on the kind of digestive enzymes.

The present invention will be illustrated more detailed in below.

Of thrombin inhibitors described in International Laid-open Publication WO 00/39124, Drug A, being a drug with a novel chemical structure, (2S)-N-{5-[amino(imino)methyl]-2-thienyl}methyl-1-{(2R)-2-[(carboxyl methyl)amino]-3,3-diphenylpropanol}-2-pyrrolidincarboxamide, was ascertained to be an orally administrable drug being well absorbed on an empty stomach, from pharmacodynamic experiments on rats and dogs. However, when Drug A was administered to dogs after ingestion of foods, the bioavailability decreased markedly (referring to FIG. 1 and TABLE 2).

Similarly to the above result, it has been reported that the change of bioavailability caused by foods also takes place with orally administered thrombin inhibitors being developed by several pharmaceutical companies.

A thrombin inhibitor, known as S-18326(Ac-D-Phe-N-cyclopentylglycine-boroArg-OH, Servier), has bioavailability of 27% when administered to a dog in the fasting state, but only 6% when administered after meals. Meanwhile, a thrombin inhibitor, known as S-31922(5-amino-1-R-(1phenethyl-carbamoyl-cyclopentane caraboxamide) pentyl boronic acid, Servier), has been reported to have bioavailability of 36% and 22%, respectively, in dogs in the fasting state and after meals, which being less affected by foods than S-18326. These two drugs have been reported to have differences in their activity to trypsin as well as thrombin; i.e., $IC_{50}$s of S-18326 and S-31922 are 3.6 nM and 43 nM to thrombin, respectively, and 20 nM and 340 nM to trypsin, respectively (Vallez M-O, Different food interaction for the orally active thrombin inhibitors S 18326 and S 31922 in dogs., XVIIth Congress of the International Society for Thrombosis and Haemostasis, Washington D.C., U.S.A., Poster 2289). Based on the fact that S-31922, with relatively low activity to trypsin, exhibits a smaller decrease in bioavailability after the ingestion of foods compared to S-18326, it can be understood that the drug with a high activity to trypsin can be further affected in view of the bioavailability.

R-Piq-Pro-Arg-H (Eli Lilly Co.), being another orally administered drug, is also well absorbed when administered orally on an empty stomach, but its bioavailability decreases remarkably in rats and human subjects after administration of foods, which has been reported (R. T. Shuman and P. D. Gesellchen, 1998, Development of an orally active tripeptide arginal thrombin inhibitor, in: Pharmaceutical Biotechnology Vol 11. Integration of Pharmaceutical Discovery and Development. p. 57–80, Plenum, N.Y.). Although its activity to trypsin has not been reported, this drug is an arginine derivative with a molecular structure similar to that of S-18326 from Servier, and the decrease of bioavailability occurs after administration of foods, thus, from these facts, it can be predicted that it will have a high activity to trypsin.

Melagatran (Glycine, N-[(1R)-2-[(2S)-2-[[[[4-(aminoiminomethyl)phenyl]-methyl]amino]carbonyl]-1-azetidinyl]-1-cyclohexyl-2-oxoethyl]-, AstraZeneca), being an orally-administered thrombin inhibitor, has also been reported to exhibit reduced bioavailability in human subjects after intake of foods. The mechanism of the reduced availability of Melagatran by the intake of foods has been reported to be based on the fact that the drug is charged under the pH condition in the intestines, and thereby the membrane penetration rate decreases. To improve this low membrane penetration rate and also reduce the effect of foods, a prodrug of Melagatran was introduced, and as a result, the bioavailability change by the altered membrane penetration rate and the bioavailability change by the intake of foods have been improved, which has been reported (D. Gustafsson et al., The direct thrombin inhibitor melagatran and its oral prodrug H376/95: Intestinal absorption properties, biochemical and pharmacodynamic effects, *Thrombosis Res.*, 101 (2001) 171–181). In addition, based on the fact that the structure of Melagatran pertains to the amidine group, being a strong basic group, it is predicted that it will exhibit a strong inhibitory action on trypsin, thus, after ingestion of foods, the bioavailability will change greatly.

Some of the thrombin inhibitors as known so far have an activity on many serine proteases in the body similar to thrombin, as indicated earlier. Trypsin, being a digestive enzyme, is also one of the serine proteases. When a drug is intended to specifically inhibit thrombin, it is desirable that it does not act on trypsin. As illustrated earlier, however, among thrombin inhibitors having a strong inhibitory effect on thrombin, many also have an activity to a certain extent on trypsin.

As known in the physiology on the digestive system, trypsin, being a digestive enzyme, is one of various digestive enzymes, such as chymotrypsin, carboxypeptidase, lipase, amylase, ribonuclease, deoxyribonuclease, etc., being secreted from the pancreas in an inactive state in response to activation of cholecystokinin (CCK), being a digestive hormone, after ingestion of foods. CCK is activated by amino acids or fatty acids present in the small intestine (V. S. Luciano, Human Physiology $5^{th}$ Ed. Chap 16 The digestion and absorption of food). Trypsin is an important digestive enzyme for proteins ingested with foods and also plays a key role in the activation of inactive digestive enzymes. After ingestion of foods, the amount of trypsin in the small intestine increases and, at this time, if a medication is administered having an activity to trypsin, the medication will be bound to trypsin depending on the activity of trypsin thereto, whereby the absorption of the medication itself will decrease. Therefore, it can be predicted that the bioavailability after intake of foods will become lower, compared to the case on an empty stomach when the concentration of trypsin is low in the small intestine, which was confirmed in Experimental Example 1.

As a result, the possibility of the food-drug interaction in vivo caused by the bonding with trypsin can be predicted by measuring the activity of the drug to trypsin in vitro and, in order to overcome the decrease of bioavailability to be caused by such food-drug interaction, methods can be suggested, such as altering the molecular structure of drug to reduce its activity to trypsin, designing the formulation of drug to reduce its activity to trypsin, etc.

This principle can also be applied to other peptidometic drugs with an activity to trypsin, as well as thrombin inhibitors. Moreover, it can be applied to other digestive enzymes having the physiological effects, as mentioned above, as well as trypsin.

In order to investigate the extent of change of bioavailability depending on the composition of foods, the bioavailability after feeding dogs on foods, i.e., starch, egg albumen and lipid, was compared with the bioavailability in the fasting state (referring to Experimental Example 1, Table 2 and FIG. 1). In this experiment, the bioavailability after feeding of the starch was not changed, compared to the fasting state, but the bioavailability after feeding of the albumin decreased remarkably (a reduction of 30% in comparison with an empty stomach) and the bioavailability after feeding of the lipid also decreased remarkably (a reduction of 48% in comparison with an empty stomach). This result can be interpreted to mean that the decrease of bioavailability was caused by increase of the trypsin amount according to the activation of pancreatic enzymes secretion by the above foods, especially, amino acid and fatty acid. It can be understood that since the starch has no significant effect on the activation of CCK and thus the increase of trypsin amount, it has no effect on the bioavailability of drug.

Meanwhile, in the case of prodrugs of Drug A disclosed in the Korean Pat. Appln. NO. 10-2002-36219, as the amidoxime or carbamate group, being able to bind to trypsin, was changed to other groups, the activity to trypsin decreased (referring to Experimental Example 2, Table 3) and the decrease of bioavailability by the foods was improved (referring to Experimental Example 3, Table 4). The chemical structure of Drug A is disclosed as blow and the chemical structures of the prodrugs 1, 2, 3 and 4 of Drug A are disclosed in the below TABLE 1.

TABLE 1

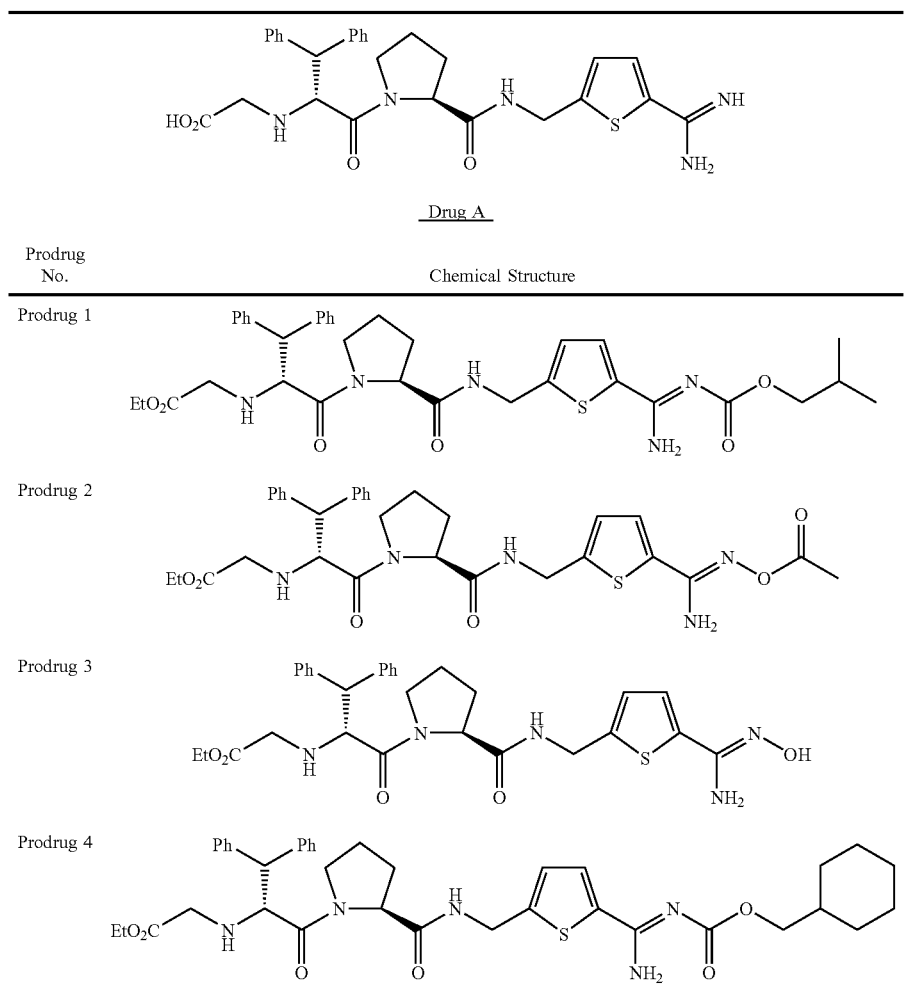

As mentioned earlier, for prodrugs of Melagatran, the mechanism of the improvement of food-drug interaction has been reported to be achieved by the improvement of membrane penetration rate (D. Gustafsson et al., The direct thrombin inhibitor melagatran and its oral prodrug H376/95: Intestinal absorption properties, biochemical and pharmacodynamic effects., Thrombosis Res., 101 (2001) 171–181); however, in the experiments involving some prodrugs of Drug A, it was shown that their bioavailability did not increase, but only the food-drug interaction was improved, so that it is difficult to say the above mechanism is achieved only by the improvement of membrane penetration rate. Herein, there is also a case that the bioavailability after feeding foods is not the same as that in the fasting state; which is because the prodrug does not react with trypsin but the absorption decreases due to the change of other properties such as solubility. However, all the prodrugs in the experiments of the present invention decreased the change of absorption rate caused by foods. This result shows that the activity to trypsin was obviated by the prodrug and the food-drug interaction was improved. Also in the case of S-18326 and S-31922 as mentioned earlier, the decrease of their absorption by foods can be improved by altering the molecular structures thereof. How much the activity to trypsin should be exactly, may depend on the type of the molecular structure of each drug. However, when the inhibition constant is in the range of hundreds of nanomole to several micromole units, it can be generally said that the activity is low. Measuring the activity to trypsin or other digestive enzymes in a test-tube, prior to the pharmacodynamic experiment on rats or dogs, can be one efficient, preliminary method for predicting the food-drug interaction in vivo caused by digestive enzymes.

The invention will be better understood with reference to the following examples which are intended for purposes of illustration and are not to be construed as in any way limiting the scope of the present invention, which is defined in the claims appended hereto.

EXPERIMENTAL EXAMPLE 1

Effect of Composition of Food on Bioavailability of Drug A in Dog

A solution in which 5 g of starch dispersed in 40 ml of water, 40 ml of egg albumin, and a solution in which 5 g of Gelucire® (44/14) dispersed in 40 ml of water, respectively, were fed to two dogs 30 minutes before administration of Drug A. These dogs (8–11 kg, Covance Research Product corporation, MI, U.S.A) were bred in a standard laboratory cage, adjusted for a temperature (22±3° C.) and humidity (50±20%), with feed and water available ad libitum. The dogs were fasted for 18–20 hours prior to this experiment. The test group for ascertaining the effect of foods was provided with foods 1 hour before administration of a drug, and the drug was administered after ingestion of foods. At a previously fixed time after administration, 500 μl of blood was gathered from the cephalic vein using the heparinized syringe, and the blood plasma was separated by a centrifuge, and then the plasma concentration of the drug was measured by HPLC analysis.

A Shiseido Capcell-Pak $C_{18}$ reverse phase column was used for the drug-detection, employing a Shimadzu HPLC system (Class-LC10A system control software, CBM-10A communication bus module, two LC-10AD pumps, SIL-10AXL autoinjector with sample cooler, SPD-10AV ultra-violet detector). The mobile phase was acetonitrile : 0.1% trifluoroacetic acid /5 mM sodium dodecyl sulfate=47 : 53 and the flow rate was 1 ml/min. Data, obtained after oral administration, was expressed in a graph of drug concentration versus time, and applied to the non-compartment model using Win-Nonlin program (Scientific Consultion Corporation, NC, U.S.A.), whereby pharmacokinetic parameters such as a half-life ($t_{1/2}$), maximum concentration ($C_{max}$), time of the maximum concentration ($T_{max}$), $AUC_{inf}$, $AUC_{last}$, and bioavailability (BA) were calculated. AUC was obtained by applying the trapezoidal rule-extrapolation method, and BA was calculated by using the formula ($AUC_{PO} \times Dose_{IV}$)/($AUC_{IV} \times Dose_{PO}$). The result of the experiment is disclosed in FIG. 1 and TABLE 2.

TABLE 2

Change (%) of Bioavailability of Drug A in Dogs Depending on Kinds of Foods

| Foods | In fasting state | After intake of starch | After intake of egg albumin | After intake of Gelucire ® |
|---|---|---|---|---|
| Bioavailability | 43 | 41 | 13 | 20 |

EXPERIMENTAL EXAMPLE 2

Measurement of Activities of Drug A and its Prodrugs to Trypsin

140 μl of 0.1 M tris buffer solution (pH 7.8) containing 150 mM NaCl and 0.1% PEG 8000 (PolyEthylene Glycol, Molecular Weight: about 8,000) was pipetted into a microplate. A substrate solution was prepared by dissolving N-benzoyl-Val-Gly-Arg-p-nitroanilide hydro-chloride in DMSO to a concentration of 10 mM, and then diluting the resultant with the above buffer solution to a concentration of 0.5 mM. 20 μl of 0.5 mM substrate solution obtained thus was added to the microplate. An inhibitor solution was prepared by dissolving the inhibitor compound according to the present invention in DMSO to make the concentration of 10 mM, and then diluting the resultant with the above buffer solution to make the concentrations of 100000 nM, 10000 nM, 1000 nM, 100 nM, 10 nM, 1 nM, 0.1 nM, 0.01 nM and 0 nM, respectively. 20 μl of each inhibitor solution was adjusted to whole volume of 180 μl and then added to the microplate.

Trypsin which had been dissolved in 0.1 N HCl solution was added to the above tris buffer, just before the experiment, to make the concentration of 1 μg/ml, and 20 μl of solution obtained thus was added to the microplate containing the reaction solution at the room temperature. The amount of para-nitroaniline produced for 10 minutes after addition of enzymes was monitored by the light. The absorbance was plotted against the reaction time. Such graphs were obtained by performing the above experiment on the various concentrations of inhibitor.

Activities of Drug A and several prodrugs to trypsin were measured by determining the dissociation constant Ki, using the following formula according to the method described in Methods in Enzymology (V.80 p341–361; Biochemistry 27 p2144–2151,1988)

$$Ki=[E] \cdot [I]/[EI]$$

[E]: concentration of enzyme not bound to inhibitor
[I]: concentration of inhibitor not bound to enzyme
[EI]: concentration of binding product of enzyme and inhibitor The dissociation constant, Ki, means the extent of dissociation of an enzyme and a trypsin inhibitor compound; therefore, the smaller the dissociation constant, the stronger the binding property of the inhibitor to the enzyme, which indicates that inhibition activity is high. Such dissociation constant can be obtained by reacting with para-nitroanilide, which is chromogenic upon hydrolysis by the action of trypsin, and then measuring the extent of chromogenicity with time by spectroscopy.

The initial velocity, Vi, was obtained from the best-fit slope for the first 30 seconds after the reaction start time for each plot, and then a graph of the concentration of inhibitor versus the inverse of the initial velocity (1/Vi) was constructed. Thereafter, the linear function, which satisfies the graph, was calculated, and then $K_i$ was calculated from the x-intercept of the above function using the enzymatic reaction formula. $K_m$ used in this calculation was obtained by changing the concentration of substrate at the constant enzyme concentration of 160 μM. The experimental results are summarized in TABLE 3.

TABLE 3

| Activities of Drug A and its Prodrugs to Trypsin | | | | | |
|---|---|---|---|---|---|
| Drug | Drug A | Prodrug 1 | Prodrug 2 | Prodrug 3 | Prodrug 4 |
| Trypsin inhibition constant (nM) | 0.30 | 673 | 21333 | 5495 | 21019 |

EXPERIMENTAL EXAMPLE 3

Effect of Ingestion of Food on Bioavailability of Drug A in Dog

Dogs (8–11 kg, Covance Research Product corporation, MI, U.S.A) were bred in a standard experimental cage, adjusted for temperature (22±3° C.) and humidity (50±20%), with feed and water available de libitum. The dogs were fasted for 18–20 hours prior to this experiment. The test group for ascertaining the effect of foods was provided with foods 1 hour before oral administration of a drug and then the drug was administered to the dogs after intake of foods. At the previously fixed time after administration, 500 μl of blood was gathered from the cephalic vein using a heparinized syringe, and the blood plasma was separated by a centrifuge, and then the plasma concentration of the drug was measured by HPLC analysis.

A Shiseido Capcell-Pak $C_{18}$ reverse phase column was used for drug-detection, employing a Shimadzu HPLC system (Class-LC10A system control software, CBM-10A communication bus module, two LC-10AD pumps, SIL-10AXL autoinjector with sample cooler, SPD-10AV ultraviolet detector). The mobile phase was acetonitrile: 0.1% trifluoroacetic acid /5 mM sodium dodecyl sulfate=47:53, and the flow rate was 1 ml/min. Data obtained after oral administration was expressed as a graph of drug concentration versus the time, and applied to the non-compartment model using Win-Nonlin program (Scientific Consultion Corporation, NC, U.S.A.), whereby PK parameters such as a half-life ($t_{1/2}$), maximum concentration ($C_{max}$), time of the maximum concentration ($T_{max}$), $AUC_{inf}$, $AUC_{last}$, and bioavailability (BA) were calculated. AUC was obtained by applying the trapezoidal rule-extrapolation method, and BA was calculated by using ($AUC_{PO} \times Dose_{IV}$)/($AUC_{IV} \times Dose_{PO}$). The bioavailability, as a result of the experiment, is disclosed in TABLE 4.

TABLE 4

Change of Bioavailability (%) by Ingestion of Foods in Dogs

| | Drug A | Prodrug 1 | Prodrug 2 | Prodrug 3 | Prodrug 4 |
|---|---|---|---|---|---|
| administration after fast | 42 | 7.1 | 28 | 28 | 0.4 |
| Administration after meals | 4.4 | 3.4 | 9 | 5 | 4 |
| Bioavailability (%) = after meals/after fast | 10 | 48 | 32 | 18 | 1000 |

Effect of the Invention

The present invention provides a novel method of predicting a food-drug interaction by measuring the interaction of a drug and enzymes, being one of the food-drug interactions, wherein the interaction of the drug and enzymes was first found by the present inventors.

On the basis of this prediction of the food-drug interaction, the present invention also provides methods of reducing the interaction of a drug and digestive enzymes, such as introduction of prodrugs, design of drug formula, etc. to improve the decrease of drug absorption be caused by intake of foods.

While there have been shown and described what are believed at the present time to be preferred embodiments of the present invention, it will be evident to one of ordinary skill in the art that various modifications may be made without departing from the scope of the invention as it is defined by the appended claims.

The invention claimed is:

1. A method of analyzing in vivo food-drug interaction of an orally administered drug comprising;
    (a) contacting the drug with one or more digestive enzymes from a gastrointestinal tract in vitro;
    (b) measuring activity of the contacted one or more digestive enzymes in vitro; and
    (c) correlating the measured activity of the one or more digestive enzymes to the in vivo food-drug interaction wherein drugs that inhibit digestive enzyme activity have an in vivo food-drug interaction.

2. The method according to claim 1, wherein said digestive enzymes are selected from the group consisting of trypsin, chymotrypsin, carboxypeptidase, lipase, amylase, ribonuclease, and deoxyribonuclease.

3. The method according to claim 1, wherein said drug is a peptidometic-based serine protease inhibitor.

4. The method according to claim 3, wherein said serine protease inhibitor is selected from the group consisting of thrombin inhibitors, Factor Xa inhibitors, and Factor VIIa inhibitors.

* * * * *